US011327138B2

(12) United States Patent
Kettinger et al.

(10) Patent No.: US 11,327,138 B2
(45) Date of Patent: May 10, 2022

(54) METHOD FOR COMPENSATING EDDY CURRENTS WHEN CREATING MEASUREMENT DATA BY MEANS OF MAGNETIC RESONANCE

(71) Applicant: Siemens Healthcare GmbH, Erlangen (DE)

(72) Inventors: Adam Kettinger, Bayern (DE); Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/034,399

(22) Filed: Sep. 28, 2020

(65) Prior Publication Data

US 2021/0096205 A1    Apr. 1, 2021

(30) Foreign Application Priority Data

Sep. 30, 2019 (DE) .......................... 102019215046.2

(51) Int. Cl.
*G01R 33/565* (2006.01)
*G01R 33/56* (2006.01)
*A61B 5/055* (2006.01)
*G01R 33/561* (2006.01)
*G01R 33/54* (2006.01)

(52) U.S. Cl.
CPC ........ *G01R 33/56518* (2013.01); *A61B 5/055* (2013.01); *G01R 33/543* (2013.01);
(Continued)

(58) Field of Classification Search
CPC .......... G01R 33/56518; G01R 33/5608; G01R 33/5616; G01R 33/543; G01R 33/56554;
(Continued)

(56) References Cited

U.S. PATENT DOCUMENTS 4,585,995 A * 4/1986 Flugan ................. G01R 33/385
324/322
6,903,550 B2 * 6/2005 Uetake ............. G01R 33/56518
324/307
(Continued)

FOREIGN PATENT DOCUMENTS

EP 1445623 A1 * 8/2004 ....... G01R 33/56518

OTHER PUBLICATIONS

Dietrich, Olaf et al. "Technical aspects of MR diffusion imaging of the body" European Journal of Radiology; vol. 76; pp. 314-322; (2010).
(Continued)

*Primary Examiner* — Susan S Lee
(74) *Attorney, Agent, or Firm* — Banner & Witcoff, Ltd.

(57) ABSTRACT

Techniques are disclosed for creating measurement data of an examination object by means of magnetic resonance technology in a plurality of repetitions according to a pulse sequence pattern, existing information about gradients that have already been switched is considered to determine compensation gradients that are possibly to be switched in a following repetition for compensating eddy current effects. Such dynamic determination and switching of compensation gradients make it possible to dynamically compensate eddy currents. Consequently, the image quality of image data reconstructed from measurement data acquired using inventive compensation gradients is increased.

11 Claims, 6 Drawing Sheets

(52) U.S. Cl.
CPC ..... *G01R 33/5608* (2013.01); *G01R 33/5616* (2013.01); *G01R 33/56554* (2013.01)

(58) Field of Classification Search
CPC .. G01R 33/56341; A61B 5/055; A61B 5/7257
See application file for complete search history.

(56) References Cited

U.S. PATENT DOCUMENTS

| | | |
|---|---|---|
| 8,508,226 B2 | 8/2013 | Feiweier et al. |
| 2021/0048498 A1* | 2/2021 | Dyvorne .......... G01R 33/56518 |

OTHER PUBLICATIONS

O'Halloran, Rafael et al. "Correction of Artifacts Caused by Transient Eddy Currents In Simultaneous Multi-Slice dMRI" ISMRM—2015, Proc. Intl. Soc. Mag. Reson. Med., 2015; Abstract No. 2931.

Setsompop, Kawin, et al.: "Blipped-controlled aliasing in parallel imaging (blipped-CAIPI) for simultaneous multislice echo planar imaging with reduced g-factor penalty"; in: Magnetic Resonance in Medicine; vol. 67,5; pp. 1210-1224; 2012; DOI 10.1002/mrm. 23097; 2012.

Breuer, Felix A. et al. "Controlled Aliasing in Parallel Imaging Results in Higher Acceleration (CAIPIRINHA) for Multi-Slice Imaging" Magnetic Resonance in Medicine, vol. 53, No. 3, pp. 684-691, 2005 // DOI: 10.1002/mrm.20401.

Chen, Feiyu et al. "Self-Calibrating Wave-Encoded Variable-Density Single-Shot Fast Spin Echo Imaging." Journal of Magnetic Resonance Imaging; 2017 // DOI: 10.1002/jmri.25853.

Gagoski, Borjan A. et al. "RARE/Turbo Spin Echo Imaging with Simultaneous Multislice Wave—CAIPI" Magnetic Resonance in Medicine; vol. 73; pp. 929-938; 2015 // DOI: 10.1002/mrm.2561.

Bilgic, Berkin et al., "Wave—CAIPI for Highly Accelerated 3D Imaging", Magnetic Resonance in Medicine, vol. 73, No. 6, pp. 2152-2162, 2015 // DOI: 10.1002/mrm.25347.

* cited by examiner

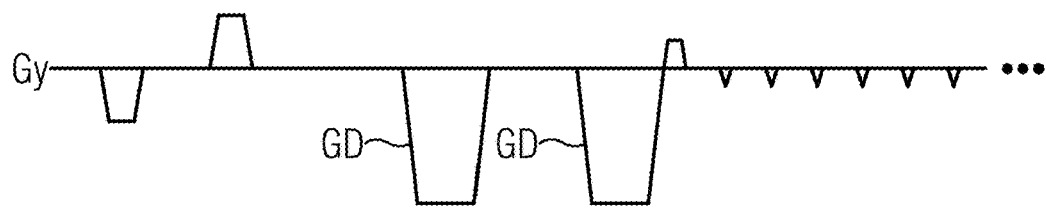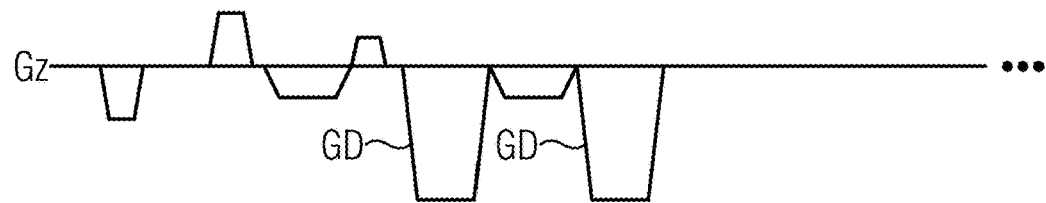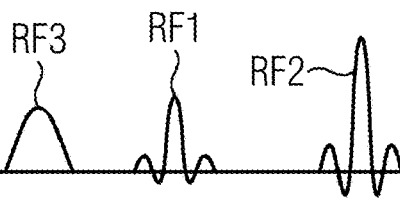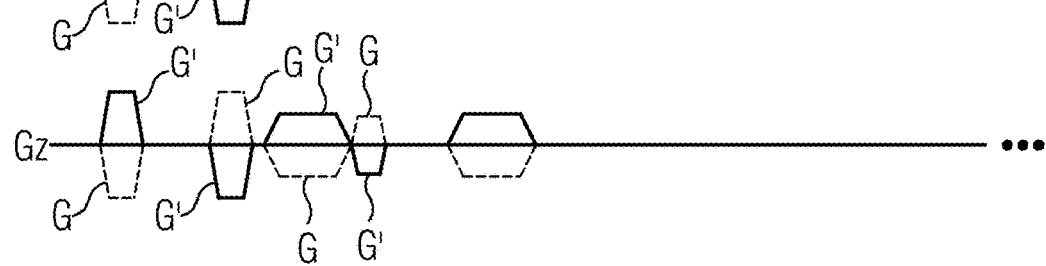
FIG 2

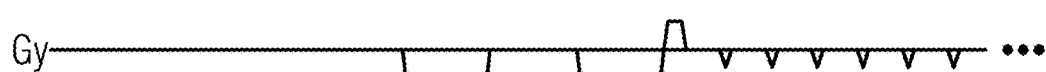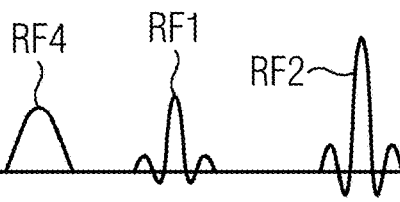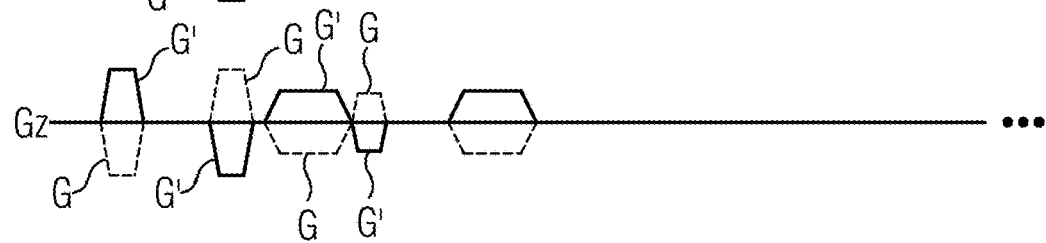

FIG 4
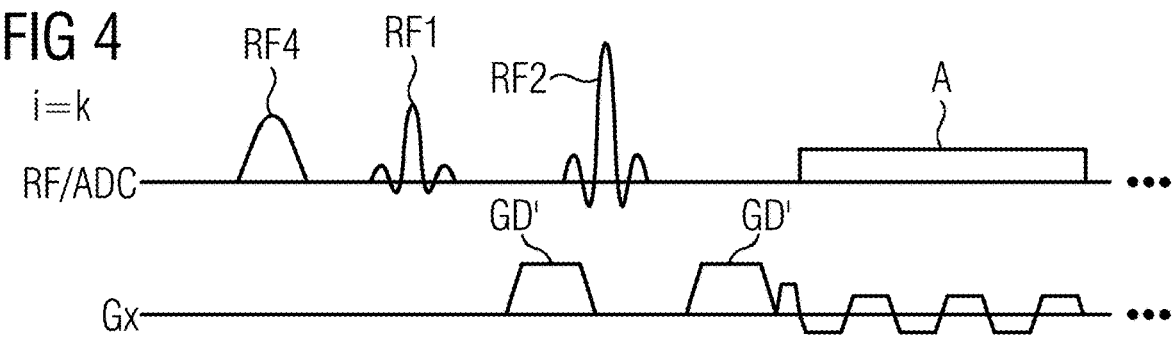
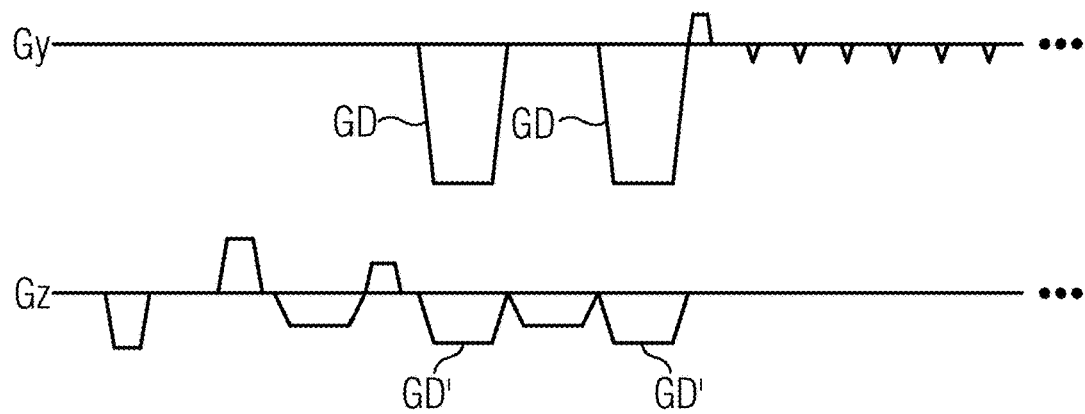
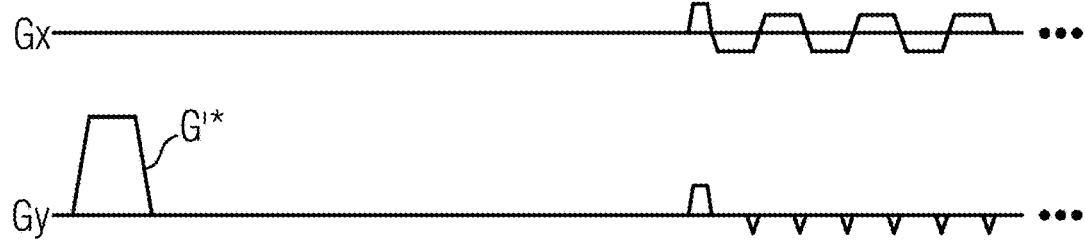
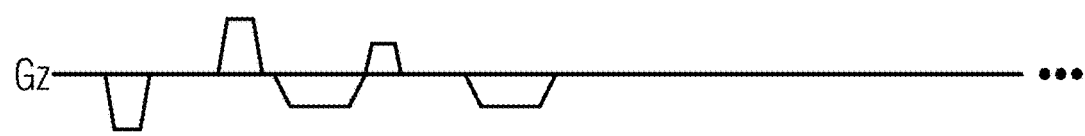

FIG 5
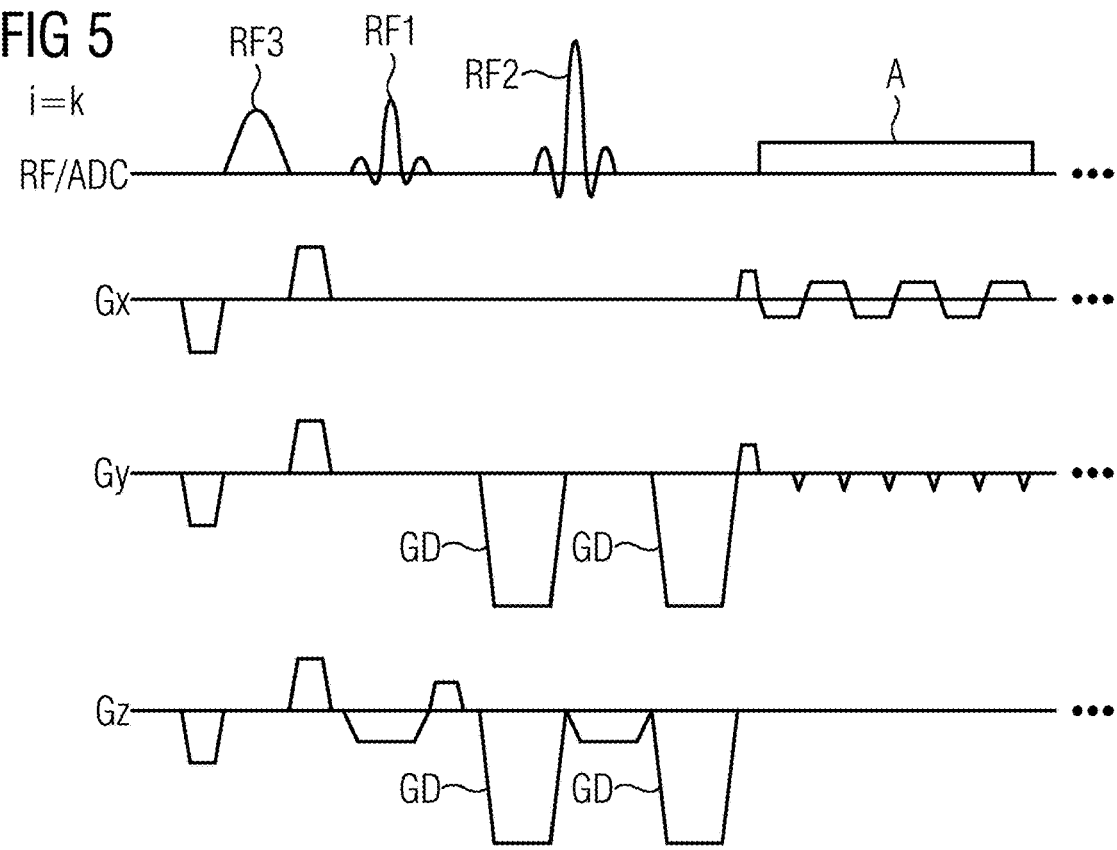
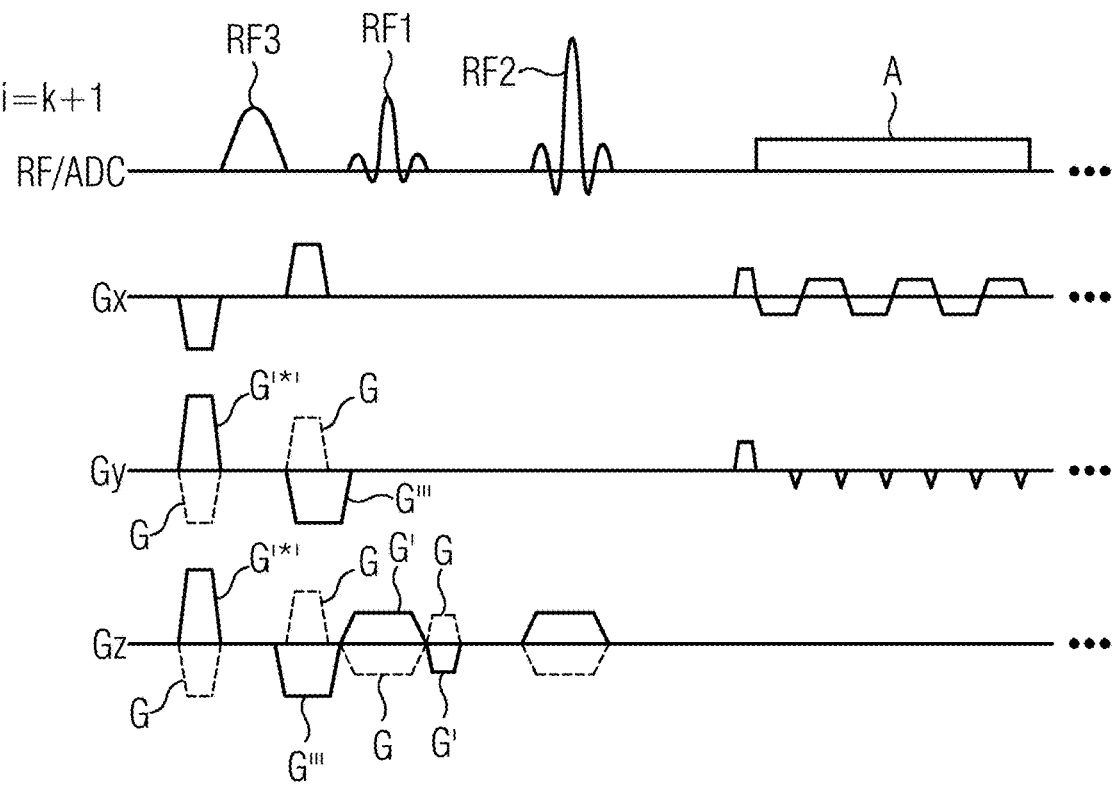

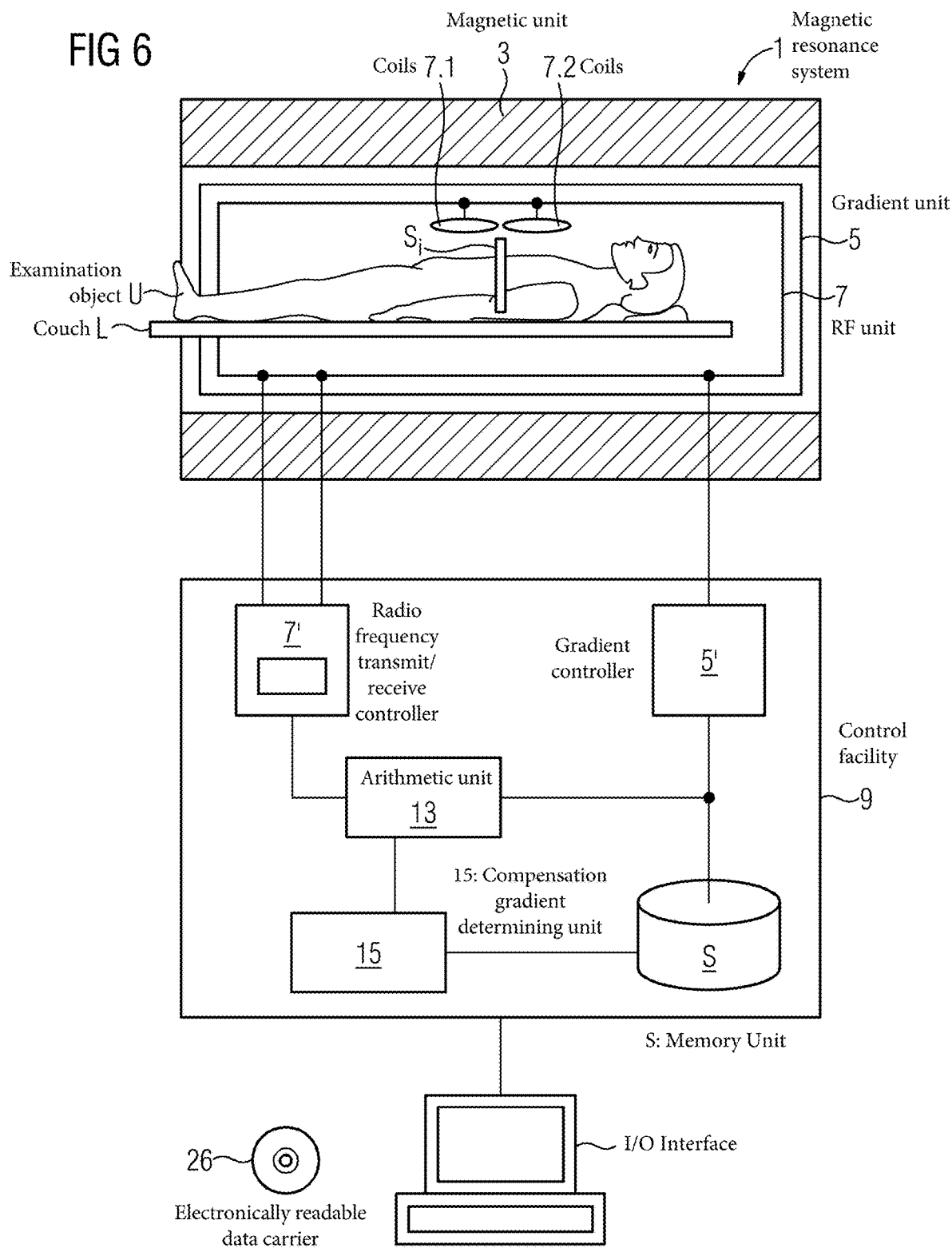

METHOD FOR COMPENSATING EDDY CURRENTS WHEN CREATING MEASUREMENT DATA BY MEANS OF MAGNETIC RESONANCE

CROSS-REFERENCE TO RELATED APPLICATIONS

The present application claims the benefit of the filing date of German patent application no DE 10 2019 215 046.2, filed on Sep. 30, 2019, the contents of which are incorporated herein by reference in their entirety.

TECHNICAL FIELD

The present disclosure relates to a method for compensating for eddy currents when creating measurement data by means of magnetic resonance, in which undesirable effects of eddy currents generated by switched gradients are prevented.

BACKGROUND

Magnetic resonance (MR) technology is a known technique with which images from inside an examination object can be generated. Put simply, the examination object is positioned for this purpose in a magnetic resonance device in a relatively strong static, homogeneous basic magnetic field, also called the B0 field, with field strengths of 0.2 tesla to 7 tesla or more, so the nuclear spins thereof are oriented along the basic magnetic field. For triggering magnetic spin resonances that can be measured as signals, radio frequency excitation pulses (RF pulses) are irradiated into the examination object, the triggered magnetic spin resonances are measured as what is known as k-space data, and MR images are reconstructed or spectroscopy data is determined on the basis thereof. For spatial encoding of the measurement data, fast-switched magnetic gradient fields, called gradients for short, are superimposed on the basic magnetic field. A pattern that is used, which describes a sequence over time of RF pulses to be irradiated and gradients to be switched, is called a pulse sequence (pattern), or sequence for short. The recorded measurement data is digitized and stored in a k-space matrix as complex numerical values. An associated MR image can be reconstructed from the k-space matrix occupied with values, for example by means of a multi-dimensional Fourier transform.

SUMMARY

A commonly-used method to generate echo signals after an excitation of the nuclear spin is what is known as the spin echo method. In the simplest case, the transverse magnetization is, as it were, "turned" by irradiating at least one RF refocusing pulse after irradiation of the RF excitation pulse, so that the de-phased magnetization is re-phased again and after a time TE called the echo time following the RF excitation pulse, what is known as a spin echo SE is generated.

The excitation and measurement of the generated echo signals are repeated after a repetition time TR (for example by switching different gradients for spatial encoding) until the desired number of echo signals has been measured and stored in the k-space to be able to depict the examination object.

Among the SE sequences, in particular the TSE sequences (TSE: "Turbo Spin Echo"), which are also known by the names FSE ("Fast Spin Echo") or RARE ("Rapid Acquisition with Refocused Echoes") sequences, are common in clinical applications. The advantage of the TSE sequences compared to the "simple" SE sequence is that, after an RF excitation pulse, a plurality of refocusing pulses are switched, and that, consequently, a plurality of spin echo signals SE are also generated after an excitation (multi-echo sequence). Therefore, data acquisition is accelerated since fewer repetitions of the sequence with different spatial encoding are required to measure all desired data. The measurement time for the entire k-space is thereby reduced in the case of TSE sequences corresponding to the number of echo signals refocused and recorded after an excitation, in what is known as the "turbofactor," compared to convention SE methods.

On the other hand, nuclear spins excited by an RF excitation pulse can be manipulated by switching de-phasing and re-phasing gradients such that the signal decays faster than the inherent T2* decay attributed to the measured tissue, but after a certain time, the echo time TE, following the RF excitation pulse, forms what is known as a measurable gradient echo. Sequences of this kind are conventionally called GRE sequences. There are also variations among the GRE sequences, which after an excitation generate a plurality of (gradient) echo signals and rank among multi-echo sequences. Mentioned as prominent variations are EPI methods ("echo planar imaging") in which an oscillating readout gradient is used, which with every change in the direction of polarization of the gradient refocuses the transverse magnetization to the extent that the T2* decay allows, and thereby generates one gradient echo in each case.

With what are known as "Single-Shot" methods, all of the k-space data to be recorded, for example for depicting a slice of an examination object to be depicted, can be recorded after just one RF excitation by an RF excitation pulse.

One example of such a Single-Shot TSE sequence is the HASTE sequence ("Half-Fourier Acquisition Single-shot Turbo spin Echo imaging") in which, to reduce the k-space data to be recorded, in addition a "partial Fourier" method, in particular the Half-Fourier method is used. The symmetry of the k-space compared to complex conjugation is used to derive non-measured k-space data from the measured k-space data. All of the k-space data of a slice to be depicted that is required for the method can be recorded thereby after just one excitation pulse. If slices of an examination objects are to be measured, for example all required k-space data of a slice can be recorded by means of HASTE after just one excitation. HASTE techniques are conventionally used for images of the thorax or abdomen, where they allow the coverage of relatively large volumes of interest (VOI) within one or more breath hold phase(s) with a reduced sensitivity compared to physiological movements of the examination object.

HASTE recording techniques are also known, inter alia, by the acronyms SS-FSE (Single-Shot Fast Spin Echo), SSH-TSE (Single-Shot Turbo Spin Echo), UFSE (Ultra-Fast Spin Echo), Single-Shot fast SE or FASE or Super-FASE (Fast Advanced Spin Echo).

The desire for ever faster MR scans in the clinical setting leads, on the other hand, to a renaissance of methods in which a plurality of images are recorded simultaneously. In general, these methods may be characterized in that, at least during part of the measurement, targeted transverse magnetization of at least two slices is used simultaneously for the imaging process ("multi-slice imaging", "slice multiplexing", "Simultaneous Multi-Slice" (SMS)). In contrast, in established "multi-slice imaging", the signal of at least two slices is recorded alternately, in other words completely independently of each other with correspondingly longer measurement time.

Known SMS methods are, for example, methods that implement techniques from parallel imaging (ppa) in which knowledge about the sensitivity distribution of the receive coils used in detecting the measurement data is used as additional information to fill measurement data subsampled according to Nyquist in the slice direction to separate superimposed signals recorded from a plurality of slices into signals of the individual slices. These methods also include, for example, the CAIPIRINHA technique, as described by Breuer et al. in "Controlled Aliasing in Parallel Imaging Results in Higher Acceleration (CAIPIRINHA) for Multi-Slice Imaging", Magnetic Resonance in Medicine 53, 2005, p. 684-691, and the blipped CAIPIRINHA technique, as is described by Setsompop et al. in "Blipped-Controlled Aliasing in Parallel Imaging for Simultaneous Multislice Echo Planar Imaging With Reduced g-Factor Penalty", Magnetic Resonance in Medicine 67, 2012, p. 1210-1224, in which the g-factor (short for "geometry factor") mentioned in the last-title represents a measure of a separability of the different receiver coils used.

As a method of reducing this g-factor further, it is also known for CAIPIRINHA methods to change the readout trajectories in the k-space, and thus the acquisition patterns, in such a way that the measurement data is acquired along wave-like or helical readout trajectories. This is described, for example, in the article by Bilgic et al. "Wave-CAIPI for Highly Accelerated 3D Imaging", Magnetic Resonance in Medicine 73:2152-2162 (2015), or for two-dimensional (2D) imaging in Chen et al. "Self-Calibrating Wave-Encoded Variable-Density Single-Shot Fast Spin Echo Imaging", J. Magn. Reson. Imaging 2018; 47:954-966, or also for Spinecho (SE)-methods in Gagoski et al. "RARE/Turbo Spin Echo Imaging with Simultaneous Multislice Wave-CAIPI", Magn. Reson. Med. 73:929-938 (2015).

Diffusion-weighted magnetic resonance (MR) images can supply important diagnostic information in the clinical routine, for example when diagnosing strokes and tumors. In diffusion-weighted imaging (DWI), diffusion gradients are switched in particular directions for preparation purposes, with the diffusion of water molecules along the applied diffusion gradient attenuating the measured magnetic resonance signal. In areas with lower diffusion there is lower signal attenuation, so these areas are depicted with higher image intensity in the case of imaging magnetic resonance tomography (MRT) measurement. The strength of the diffusion weighting is correlated with the strength of the applied diffusion gradients in this case. The diffusion weighting can be characterized by what is known as the b-value, which is a function of gradient parameters, such as the gradient strength, duration or interval between the applied diffusion gradients. Owing to the speed of these sequences, the resulting magnetic resonance signals are usually recorded with a multi-echo sequence, such as EPI.

In diffusion imaging, as a rule, a plurality of images with different diffusion directions and weightings (characterized by the b-value) are recorded and combined with each other in order to calculate, for example, diffusion parameter maps, in particular the diffusion parameter "Apparent Diffusion Coefficient" (ADC) and/or "Fractional Anisotropy" (FA). An overview of known DWI methods is given in the review article by Dietrich et al., "Technical aspects of MR diffusion imaging of the body", European Journal of Radiology 76, p. 314-322, 2010.

As stated above, slice multiplexing methods make the measurement of echo signals from two or more slices simultaneously, possible within one measurement data acquisition. Consequently, in multi-echo methods in which, after a first excitation of spins, a plurality of echo signals are generated and recorded by these methods by irradiation of RF pulses and/or switching of gradients, the minimum repetition time TR can be reduced compared to single slice measurements, which is required for recording all desired echo signals after a first excitation since fewer echo signals have to be generated if they are recorded from a plurality of slices simultaneously than if each recorded echo signal contains only measurement data of a single slice. For example, if measurement data is measured from n slices simultaneously, the time required for recording the desired echo signals of all slices is reduced by the factor n.

One problem with the current MR methods are eddy currents, which result due to gradients to be switched, and can lead to off-resonance effects and other artifacts. Methods are already known for retrospectively compensating for these kinds of artifacts caused by eddy currents using additionally recorded reference data. One such method is described, for example, in issued U.S. Pat. No. 8,508,226.

While the eddy currents caused by a switched gradient do decay again, the stronger a switched gradient is (in other words, the greater its amplitude), the longer it takes until the eddy currents have decayed. Therefore, undesirable eddy current effects occur predominantly in sequences that require strong gradients, such as in diffusion imaging for high diffusion values b, or else also in TSE sequences or HASTE sequences with strong gradients during the reading out process for fast recording of the measurement data if a further manipulation of spins and/or recording of measurement data occurs after a preceding strong gradient whose eddy currents that it has caused have not yet decayed.

In the article by O'Halloran et al. "Correction of Artifacts Caused by Transient Eddy Currents in Simultaneous Multi-Slice dMRI", Proc. Intl. Soc. Mag. Reson. Med. 23 (2015) p. 2931, this problem is explained with reference to diffusion imaging and a retrospective method proposed to correct the disruptive artifacts.

The disclosure is directed to aspects that have the object of enabling accelerated acquisition of measurement data by means of magnetic resonance in which undesirable eddy current effects are prevented as early as during acquisition of the measurement data.

The object is achieved by a method for creating measurement data of an examination object by means of magnetic resonance technology in a plurality of repetitions according to a pulse sequence pattern, a magnetic resonance system, a computer program, and an electronically readable data carrier as described throughout the disclosure and in the claims.

In an aspect, a method for creating measurement data of an examination object by means of magnetic resonance technology in a plurality of repetitions according to a pulse sequence pattern, comprises the following steps:

loading a measurement protocol, with which the measurement data is to be acquired, which comprises a pulse sequence pattern to be used and planned gradients to be applied in successive repetitions of the pattern, acquiring measurement data according to the measurement protocol, wherein after each repetition it is checked whether at least one gradient was switched in the repetition just carried out whose amplitude exceeds a predefined threshold value, and if yes (if at least one gradient, whose amplitude exceeds the predefined threshold value, was switched in a repetition just carried out), at least one compensation gradient is determined, which is switched in a repetition that follows the repetition with the at least one gradient that exceeds the threshold value, reconstructing image data from the acquired measurement data.

The determination and switching of compensation gradients compensate eddy current effects caused by gradients switched before the compensation gradients timewise, so that there is at least a reduction in such eddy current effects as early as prospectively during recording of measurement data.

Available information about gradients already switched (e.g. at least above a predefined threshold value) are considered in this case to determine compensation gradients that are possibly to be switched in a repetition to compensate eddy current effects. Such dynamic determination and switching of compensation gradients make it possible for eddy currents to be dynamically compensated. Consequently, the image quality of image data reconstructed from measurement data recorded using the compensation gradients described in accordance with the aspect herein is increased.

In an aspect, a magnetic resonance system is provided comprising a magnetic unit, a gradient unit, a radio frequency unit, and a control facility, designed to carry out the aspects of the method(s) described herein, using a compensation gradient determining unit.

In an aspect, a computer program is provided implementing the aspects of the method(s) described herein, on a control facility (e.g. a controller, control computer, control circuitry, etc.) when it is run on the control facility.

The computer program can also be in the form of a computer program product (e.g. a non-transitory computer-readable medium), which can be loaded directly into a memory of a control facility, with program code means to carry out the aspects of the method(s) when the computer program product is run in an arithmetic unit, for instance, of a data processing system or otherwise executed via the control facility.

In an aspect, an electronically-readable data carrier is provided comprising electronically readable control information stored thereon, which comprises at least one of the computer programs in accordance with re aspects described herein and is configured in such a way that it carries out the aspects of the method(s) when the data carrier is used in a control facility of a magnetic resonance system.

The advantages and statements disclosed in relation to the method also apply analogously to the magnetic resonance system, the computer program product, and the electronically readable data carrier.

BRIEF DESCRIPTION OF THE DRAWINGS/FIGURES

Further advantages and details of the present disclosure can be found in the exemplary embodiments described below and with reference to the drawings. The stated examples do not represent a limitation of the disclosure. In the drawings:

FIGS. 2-5 show schematically illustrated parts of example pulse sequence patterns for acquiring measurement data with compensation gradients, in accordance with one or more aspects of the present disclosure; and FIG. 6 shows a schematically illustrated example magnetic resonance system, in accordance with one or more aspects of the present disclosure.

DETAILED DESCRIPTION

Figure 1:
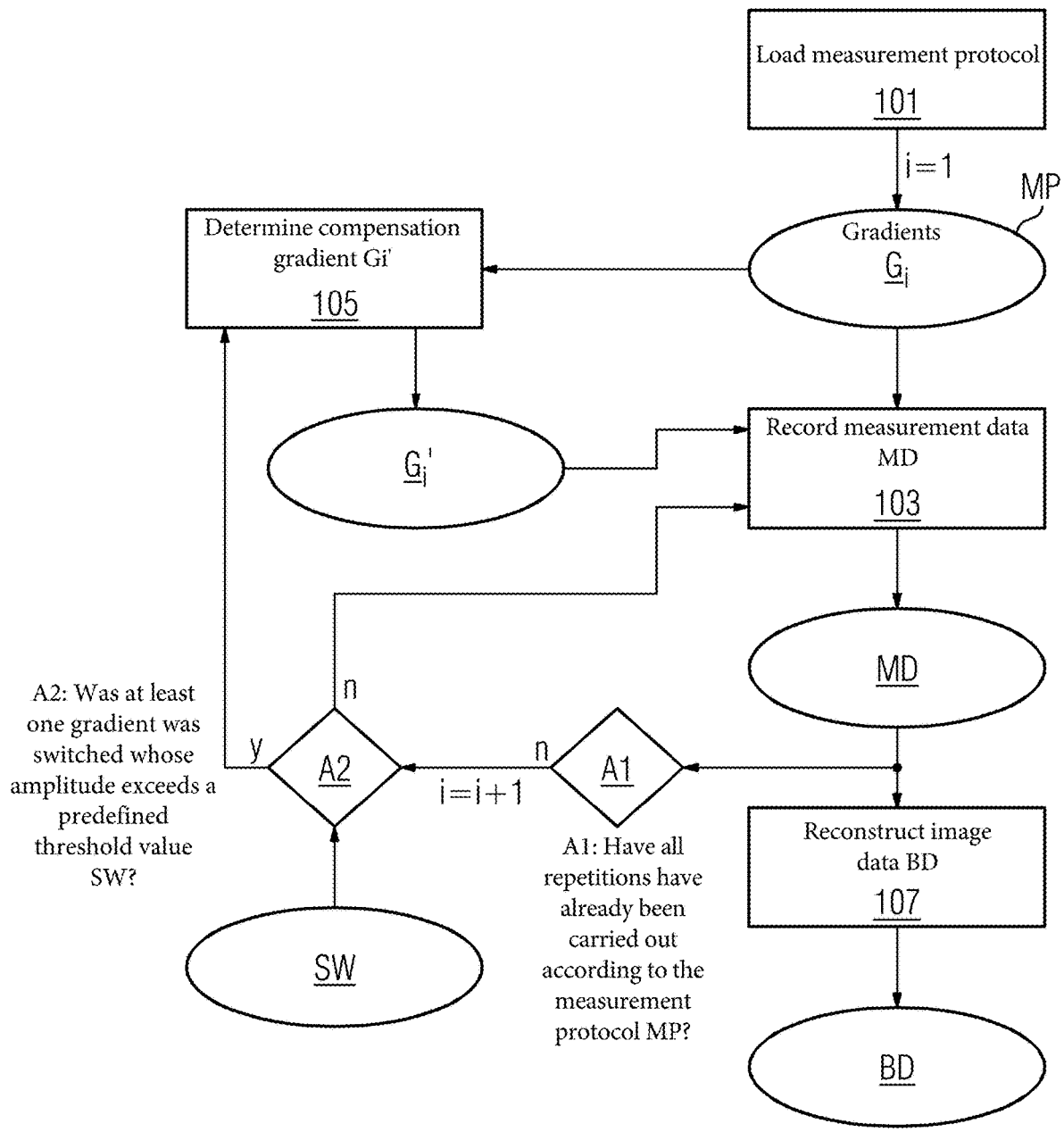
FIG. 1 shows an example of a flow, in accordance with one or more aspects of the present disclosure.

FIG. 1 is an example flow of a method for creating measurement data of an examination object by means of magnetic resonance technology in a plurality of repetitions according to a pulse sequence pattern.

Firstly, a measurement protocol (MP) is loaded (block 101) with which the measurement data is to be recorded. The measurement protocol MP comprises a pulse sequence pattern that is to be used and planned gradients $G_i$ that are to be applied in successive repetitions i thereof.

According to the measurement protocol, measurement data MD is recorded (block 103), wherein, provided nothing else results (see query A2 and block 105 further below), the planned gradients $G_i$ are applied.

After a recording of measurement data MD that has occurred during the course of a repetition i, it can be established by means of a query A1 whether all repetitions have already been carried out according to the measurement protocol MP. If this is the case, the method ends. If not all repetitions have been carried out yet according to the measurement protocol MP (query A1, "n"), the counter of the repetitions is increased by one ("i=i+1") and it is checked, for example by way of a query A2, whether in the repetition just carried out at least one gradient was switched whose amplitude exceeds a predefined threshold value SW.

If this is not the case (query A2, "n"), measurement data MD continues to be is recorded in the following repetition with the gradients planned according to measurement protocol MP.

If this is the case, since at least one gradient, whose amplitude exceeds the predefined threshold value SW, was switched in the repetition last carried out, at least one compensation gradient $G_i'$ is determined, which is switched in a following repetition i+1 (block 105), for example in the one that directly follows the repetition i with the at least one gradient that exceeds the threshold value SW.

The choice of threshold value SW can be made not only as a function of the amplitude of the switched gradients, but also as a function of a time interval of a switched gradient from a manipulation of spins in the target volume, from which measurement data is recorded, in a subsequent repetition, e.g. considering a decay behavior of eddy currents in such a way that when the threshold value SW is maintained, no disruptive eddy current effects are to be expected in the immediately following repetition. In addition or as an alternative, the threshold value SW can also consider the amplitudes of the gradients planned in the subsequent repetition, and can be chosen as a function of these amplitudes in such a way that a maximum difference in the amplitudes of the preceding repetition i and the amplitudes of the subsequent repetition i+1 is not exceeded, wherein the maximum difference can in turn be chosen in such a way that it should be anticipated that eddy current effects caused by the gradients of the preceding repetition i play no part, or only a small part, in the course of the subsequent repetition i+1.

From the recorded measurement data MD, image data BD can be reconstructed (block 107), which can be stored, for example, in a memory for later use or processing and/or displayed to a user on a display device (e.g. an input/output facility of a magnetic resonance system) that is used.

In an aspect, determination of compensation gradients $G_i'$ can comprise a reversal of the polarity of gradients $G_i$ planned for the following repetition.

FIG. 2 illustrates an example of this kind of determination of compensation gradients and schematically shows parts of pulse sequence patterns for acquiring measurement data MD with compensation gradients.

The upper region of FIG. 2 shows a pulse sequence pattern in its course over time that is to be carried out according to measurement protocol for a repetition i=k. The top rows RF/ADC illustrate the RF pulses RF1, RF2, RF3 to be irradiated and the readout period A in which the measurement data is recorded.

In the illustrated example, after an RF excitation pulse RF1, a RF refocusing pulse RF2 is irradiated to excite the spins in the target volume and generate echo signals, which are recorded in the readout period A. Furthermore, the example of FIG. 2 shows a preparation pulse RF3, which is irradiated before the RF excitation pulse RF1, and can serve, for example, to saturate fatty fractions.

The further rows show the gradients to be switched in the readout direction Gx, phase encoding direction Gy, and slice encoding direction Gz. Spoiler gradients are switched before and after the preparation pulses RF3 here in all gradient directions Gx, Gy, Gz. The illustrated pulse sequence pattern corresponds with its typical gradient in the readout direction Gx during the readout period A to an EPI pulse sequence.

Strong gradients GD, as are used, for example, in diffusion imaging, are shown in the gradient directions Gy and Gz. These gradients GD exceed the predefined threshold value, for which reason the compensation gradients G' shown by way of example were determined for the following repetition i=k+1 (shown at the bottom of FIG. 2) in that the polarity of the gradients G planned for the repetition i=k+1 was reversed to obtain the compensation gradients $G_i'$.

The repetition i=k+1 corresponds to the preceding repetition i=k apart from the compensation gradients G' and the strong gradients GD, which are switched only in the preceding repetition i=k, but not in the subsequent repetition i=k+1.

The reversal of the polarity of the gradients G planned for the repetition i=k+1 counteracts eddy current effects caused by the gradients GD in a simple manner A reversal of the polarity is possible without any great difficulties and in particular has no effects on the course over time of the pulse sequence patterns or the gradient unit generating the gradients, so that no disruptions due to the compensation gradients G' should be anticipated. A reversal of a polarity is easily possible without computing effort and already provides good compensation of eddy current effects.

In the example shown in FIG. 2, only the polarity of the gradients G planned for the following repetition i=k+1, which are switched in the same direction Gy, Gz as a previously switched gradient GD that exceeds the threshold value, is reversed to obtain compensation gradients G'. In this way, a change in the measurement protocol that is to be implemented by the compensation gradients G' is kept to a minimum. Furthermore, eddy current effects should primarily be anticipated in the gradient directions in which gradients, which exceed the threshold value SW, were switched, so that no equally clear reduction in eddy current artifacts should be anticipated by further compensation gradients G' in other directions, in which no gradient, which exceeds the threshold value, was switched.

In principle, the gradients switched during the readout period A can also have their polarity reversed to compensate eddy current effects in the readout direction Gx. This should be considered in particular for types of sequence such as HASTE in which a reversal of the polarity of the readout gradients switched during a readout period A, does not generate disruptive secondary effects. For certain types of sequence, in particular for example with EPI sequences, undesirable secondary effects, such as phase errors, should be anticipated in the recorded measurement data, however, if the polarity of the gradients switched in the readout direction is changed in different repetitions.

In addition or as an alternative, determination of compensation gradients G' can comprise adding additional gradients G" to the gradients planned for the following repetition.

FIG. 3 illustrates one example of such a determination of compensation gradients, and schematically shows parts of pulse sequence patterns for acquiring measurement data MD with compensation gradients G', G".

Analogously to FIG. 2, the upper region of FIG. 3 shows a pulse sequence pattern that is to be implemented according to measurement protocol in its course over time for a repetition i=k. The top row RF/ADC illustrates the RF pulses RF1, RF2, RF4 to be irradiated and the readout period A in which the measurement data is recorded. The further rows again show the gradients to be switched in the readout direction Gx, phase encoding direction Gy, and slice encoding direction Gz.

In contrast to FIG. 2, a different preparation pulse RF4 is shown, for example a SPAIR pulse (SPAIR: "spectral adiabatic inversion recovery"), which is conventionally framed by spoiler gradients only in the slice selection direction Gz. Otherwise, the repetition i=k in FIG. 3 corresponds to the repetition i=k in FIG. 2.

Strong gradients GD, as are used, for example, in diffusion imaging, are again switched in FIG. 3 in repetition i=k in the gradient directions Gy and Gz. These gradients GD exceed the predefined threshold value, for which reason for the following repetition i=k+1 (shown at the bottom of FIG. 3) in the slice selection direction Gz, the compensation gradients G' shown by way of example were determined in that the polarity of the gradients G planned for the repetition i=k+1 were reversed to obtain the compensation gradients $G_i'$ and in that additional gradients G" are switched in the phase encoding direction Gy, in other words, in the same direction as a previously switched gradient GD that exceeds the threshold value. The additional gradients G" are arranged as further spoiler gradients before and after the preparation pulse RF4 and have a vanishing zeroth moment. In this way, the additional gradients G", and therewith all compensation gradients G' and G", do not have any effect on the course over time of the pulse sequence patterns either and do not cause any difficulties in their implementation.

The repetition i=k+1 corresponds here to the preceding repetition i=k apart from the compensation gradients G' and G", and the strong gradients GD, which are switched only in the preceding repetition i=k but not in the subsequent repetition i=k+1.

In addition or as an alternative, determination of compensation gradients can comprise adjustment of amplitude and/or duration of gradients planned for the following repetition i=k+1.

FIG. 4 illustrates one example of such a determination of compensation gradients, and schematically shows parts of pulse sequence patterns for acquiring measurement data MD with inventive compensation gradients G'*.

Analogously to FIGS. 2 and 3, the upper region of FIG. 4 illustrates a pulse sequence pattern to be implemented according to measurement protocol in its course over time for a repetition i=k. The top row RF/ADC shows the RF pulses RF1, RF2, RF4 to be irradiated and the readout period A in which the measurement data is recorded. The further rows again show the gradients to be switched in the readout direction Gx, phase encoding direction Gy, and slice encoding direction Gz.

As already in FIG. 3, a preparation pulse RF4 is illustrated here, for example a SPAIR pulse (SPAIR: "spectral adiabatic inversion recovery"), which is conventionally framed by spoiler gradients only in the slice selection direction Gz. In contrast to the repetition i=k in FIG. 3, in FIG. 4 only strong gradients GD, which exceed the threshold value, are switched in the phase encoding direction Gy in the repetition i=k, however. While gradients GD' are likewise simultaneously switched in the gradient directions Gx and Gz, in the illustrated example these do not exceed the predefined threshold value.

Additional gradients G'* (in the illustrated example, an additional gradient G'*) were switched only in the gradient direction Gy as the compensation gradient G'* for the following repetition i=k+1 (shown at the bottom of FIG. 4), therefore. The additional gradient G'* is arranged before the preparation pulse RF4 timewise and compensates eddy current effects generated by the gradients GD switched in the previous repetition i=k in phase encoding direction Gy. The additional gradient G'* has an effect on the course over time of the pulse sequence pattern and has to be switched in a sufficient time interval from the readout period A of the repetition i=k+1 that eddy current effects generated by the compensation gradients G'* have decayed as far as possible at a starting instant of the readout period A. It can be expedient for each gradient direction, in which in a preceding repetition a gradient was switched, which exceeds the threshold value, to switch an additional gradient G'* even if the course over time of the pulse sequence is affected thereby, because a gradient direction affected per amplitude and duration of such a compensation gradient as an additional gradient G'* can be easily determined in such a way that an additional gradient G'* accurately compensates the respective eddy current effects. Further information on this will be given below in which a calculation method for compensation gradients is presented.

Since no gradients, which exceed the predefined threshold value, are switched in the slice selection direction Gz and in readout direction Gx in the repetition i=k in FIG. 4, no compensation gradients are switched in these gradient directions Gz and Gx in the repetition i=k+1 to keep the stress on the gradient unit low.

In addition or as an alternative, determination of compensation gradients can comprise an adjustment of amplitude and/or duration of gradients planned for the following repetition i=k+1.

FIG. 5 illustrates one example of such a determination of compensation gradients and schematically shows parts of pulse sequence patterns for acquiring measurement data MD with compensation gradients G'*', G'''.

Analogously to FIGS. 2 to 4, the upper region of FIG. 5 illustrates a pulse sequence pattern to be implemented according to measurement protocol in its course over time for a repetition i=k. The top row RF/ADC shows the RF pulses RF1, RF2, RF3 to be irradiated and the readout period A in which the measurement is recorded. The further rows again show gradients to be switched in the readout direction Gx, phase encoding direction Gy, and slice encoding direction Gz. The repetition i=k illustrated in FIG. 5 corresponds to the repetition i=k illustrated in FIG. 2, for which reason reference is made to the above description thereof.

The strong gradients GD switched in the gradient directions Gy and Gz in the repetition i=k exceed the predefined threshold value and cause undesirable eddy current effects, therefore, which are to be compensated in the following repetition i=k+1. For this, the compensation gradients G', G'*', and G''' shown by way of example, which were determined in that the polarity of gradients G planned for the repetition i=k+1 is reversed (to obtain the compensation gradients G'), and their amplitude and/or duration was possibly adjusted (to obtain the compensation gradients G'*' and G''', which are switched before and after the preparation pulse RF3), are switched in the following repetition i=k+1 (shown at the bottom of FIG. 5).

The compensation gradients G'*' and G''', whose amplitude and/or duration was changed, together have a vanishing zeroth moment here, so that they have no effect on the phases of the measurement data recorded in the readout window A. Advantageously, the amplitude of the compensation gradient G'*', switched before the preparation pulse RF3, is increased compared to the gradient G planned at this instant to increase the compensation effect of the compensation gradient G'*', and the amplitude of the compensation gradient G''' switched after the preparation pulse RF3 is reduced compared to the gradient G planned at this instant and it duration is lengthened compared to the gradient G planned at this instant, so that the compensation effect achieved by switching the compensation gradients G', G'*', and G''' is, as far as possible, not reversed. In particular, a compensation pulse G''' lengthened in its duration can result in the course over time of the pulse sequence being affected.

In addition or as an alternative, determination of compensation gradients can comprise an optimization method for determination of optimum compensation gradients for compensation of an eddy current effect generated by the at least one gradient that exceeds the threshold value.

In general terms, the moments, durations, and/or amplitudes of compensation gradients to be switched can be expressly calculated for example by assuming an exponential drop in eddy current effects scaled with an amplitude of a switched gradient, and compensation gradients determined by an optimization method that, for example, minimizes the total number of gradients already switched and calculated under the above assumption and compensation gradients to be determined for each gradient direction Gx, Gy, Gz. Compensation gradients determined in this way optimally compensate eddy current effects generated by gradients that have already been switched.

This can be expressed in Equation 1 below as follows:

$$\min_{G_{comp}(\kappa)} \left| \sum_{j=1}^{n} G_{diff}(j)\, e^{\frac{t_{diff}(j)-t_{event}}{\tau}} + \sum_{\kappa=1}^{m} G_{comp}(\kappa)\, e^{\frac{t_{comp}(\kappa)-t_{event}}{\tau}} \right|, \quad \text{Eqn. 1}$$

in which $G_{diff}(j)$ indicates the amplitudes of all n relevant gradients already switched, wherein, according to the desired level of accuracy, all gradients already switched or, to simplify the calculation, for example only gradients above a predefined minimum amplitude (e.g. diffusion gradients for a diffusion preparation with a high diffusion value b), are considered. Further, $t_{diff}(j)$ indicates the instant at which a gradient $G_{diff}(j)$ being considered was switched. Moreover, $t_{event}$ indicates the instant at which influence of the eddy current effect generated by the gradients $G_{diff}(j)$ being considered is to be minimized, in particular optimally completely compensated (for example at a starting instant of a readout period). κ represents the decay constant with which eddy current effects decay. $G_{comp}(\kappa)$ and $t_{comp}(\kappa)$ are the amplitude and the instant of the m compensation gradients to be determined, respectively.

As boundary conditions for the optimization it can be demanded, for example, that the course over time of a pulse sequence that is being used should not change and/or that an overall gradient moment should be maintained in a gradient direction and/or the instants $t_{comp}(\kappa)$ at which compensation gradients are allowed to be switched are defined.

Such an optimization can be used for optimized compensation of different eddy current effects. For example, if displacement or compression artifacts caused by eddy current effects are to be compensated as optimally as possible, an instant can be chosen as instant $t_{event}$ at which the measurement data is recorded in a central k-space region (for example the instant, which the echo time TE lies at after an excitation).

If, for example, a suppression of undesirable signals (e.g. of fat signals), is, as far as possible, not falsified by eddy current effects, the instant at which, for example, a corresponding preparation pulse (e.g. a fat suppression pulse), is irradiated can be chosen as the instant $t_{event}$.

The loaded measurement protocol MP can in particular predefine an EPI (diffusion) pulse sequence or a HASTE pulse sequence (with at least one strong gradient that exceeds a predefined threshold value in the readout direction) or a TSE pulse sequence (with at least one strong gradient that exceeds a predefined threshold value in the readout direction) as the pulse sequence.

FIG. 6 schematically illustrates a magnetic resonance system 1 in accordance with one or more aspects of the present disclosure. The magnetic resonance system 1 comprises a magnetic unit 3 for generating the basic magnetic field, a gradient unit 5 for generating the gradient fields, a radio frequency unit 7 for irradiating and receiving radio frequency signals, and a control facility 9 (e.g. one or more processors such as a controller, control computer, control circuitry, etc.) configured to execute one or more of the aspects related of the method(s) described herein.

FIG. 6 illustrates these sub-units of the magnetic resonance system 1 schematically. In particular, the radio frequency unit 7 can comprise a plurality of sub-units, for example a plurality of coils, such as the schematically illustrated coils 7.1 and 7.2 or more coils, which can be configured only to transmit radio frequency signals or only to receive the triggered radio frequency signals, or to do both.

To examine an examination object U, for example a patient or also a phantom, the object can be introduced on a couch L into the magnetic resonance system 1, into the measurement volume thereof. The slice or the slab $S_i$ constitutes an exemplary target volume of the examination objects from which data is to be recorded and acquired as measurement data.

The control facility 9 serves to control the magnetic resonance system 1 and can control, in particular, the gradient unit 5 by means of a gradient controller 5' and the radio frequency unit 7 by means of a radio frequency transmit/receive controller 7'. The radio frequency unit 7 can comprise a plurality of channels on which signals can be transmitted or received.

The radio frequency unit 7, together with its radio frequency transmit/receive controller 7' is responsible for generating and irradiating (transmitting) a radio frequency alternating field for manipulation of the spins in a region to be manipulated (for example in slices S to be measured) of the examination object U. The center frequency of the radio frequency alternating field, also called the B1 field, is, as a rule, optimally adjusted such that it is close to the resonance frequency of the spins to be manipulated. Deviations of the center frequency from the resonance frequency are called off resonance. Currents controlled by means of the radio frequency transmit/receive controller 7' are applied to the RF coils to generate the B1 field in the radio frequency unit 7.

The control facility 9 also comprises a compensation gradient determining unit 15 with which inventive compensation gradients can be determined for the compensation of eddy currents, which can be implemented by the gradient controller 5'. As a whole, the control facility 9 may include one or more processors, processing circuitry, or any suitable type of computing components to execute one or more of the aspects related of the method(s) described herein.

An arithmetic unit 13 encompassed by the control facility 9 is designed to carry out all arithmetic operations necessary for the required measurements and determinations. Intermediate results required for this or determined in this connection can be stored in a memory unit S of the control facility 9. The illustrated units should not necessarily be taken to mean physically separate units here, instead they merely represent a division into meaningful units, but they can also be implemented for example in fewer or also in just a single physical unit.

Control commands can be passed via an input/output facility (e.g. I/O interface) of the magnetic resonance system 1, for example by a user, to the magnetic resonance system and/or results of the control facility 9 such as image data can be displayed.

The aspects of the method(s) described herein can also be in the form of a computer program product (e.g. a non-transitory computer-readable medium), which comprises a program and implements the described aspects in accordance with the method(s) herein on a control facility 9 when it is executed on the control facility 9 or components associated therewith to facilitate the magnetic resonance system 1 executing one or more of the aspects related of the method(s) described herein. Similarly, there can be an electronically readable data carrier 26 with electronically readable control information stored thereon, which comprises at least one such computer program product just described and is configured in such a way that it carries out one or more of the aspects related of the method(s) described herein when the data carrier 26 is used in a control facility 9 of a magnetic resonance system 1.

The various functional blocks, apparatuses, modules, units, components of physical or functional units, etc., as shown in the drawings and described herein may be implemented unless otherwise noted via any suitable number and type of computer processors, hardware components, the execution of software algorithms, or combinations thereof, and thus may alternatively be referred to as a "unit," "system," "circuitry," or "device."

What is claimed is:

1. A method for acquiring data of an examination object using magnetic resonance (MR) imaging, comprising:
loading, via one or more processors, a measurement protocol for acquiring data of the examination object, the measurement protocol indicating a pulse sequence pattern and gradients to be applied in successive repetitions of the pulse sequence pattern;
acquiring, via one or more processors, measurement data according to the measurement protocol by (i) determining, after each one of the successive repetitions in which a previous repetition included at least one gradient having an amplitude exceeding a predefined threshold value, at least one compensation gradient, and (ii) applying, via the one or more processors, the at least one compensation gradient following each one of the previous successive repetitions that included the at least one gradient having an amplitude exceeding the predefined threshold value; and reconstructing, via one or more processors, image data using the acquired measurement data.

2. The method as claimed in claim 1, wherein the determination of the at least one compensation gradient comprises a reversal of a polarity of a gradient following a previous successive repetition that included the at least one gradient having an amplitude exceeding the predefined threshold value as indicated by the measurement protocol.

3. The method as claimed in claim 2, wherein the at least one compensation gradient is applied in the same direction as the at least one gradient having an amplitude exceeding a predefined threshold value.

4. The method as claimed in claim 1, wherein the at least one compensation gradient is from among a plurality of gradients including the at least one compensation gradient and additional gradients.

5. The method as claimed in claim 4, wherein the additional gradients are switched in the same direction as the at least one gradient having an amplitude exceeding the predefined threshold value.

6. The method as claimed in claim 4, wherein the additional gradients have a vanishing zeroth moment.

7. The method as claimed in claim 1, wherein the determination of the at least one compensation gradient comprises an adjustment of at least one of an amplitude and a duration of at least one gradient following a previous successive repetition that included the at least one gradient having an amplitude exceeding the predefined threshold value as indicated by the measurement protocol.

8. The method as claimed in claim 1, wherein the determination of the at least one compensation gradient comprises determining an optimum compensation gradient for compensation of an eddy current effect generated by the at least one gradient having an amplitude exceeding the predefined threshold value.

9. The method as claimed in claim 1, wherein the pulse sequence defined in accordance with the measurement protocol includes one of an echo planar imaging (EPI) diffusion pulse sequence, a Half-Fourier Acquisition Single-shot Turbo spin Echo imaging (HASTE) pulse sequence, or a Turbo Spin Echo (TSE) pulse sequence.

10. A magnetic resonance system, comprising:
a magnet;
gradient circuitry;
radio frequency (RF) circuitry; and
a controller configured to:
    load a measurement protocol for acquiring data of an examination object, the measurement protocol indicating a pulse sequence pattern and gradients to be applied in successive repetitions of the pulse sequence pattern,
    acquire measurement data according to the measurement protocol by (i) determining, after each one of the successive repetitions in which a previous repetition included at least one gradient having an amplitude exceeding a predefined threshold value, at least one compensation gradient, and (ii) applying, via the one or more processors, the at least one compensation gradient following each one of the previous successive repetitions that included the at least one gradient having an amplitude exceeding the predefined threshold value; and
    reconstruct image data using the acquired measurement data.

11. A non-transitory computer-readable medium having instructions stored thereon that, when executed by a controller associated with a magnetic resonance (MR) apparatus for acquiring data of an examination object using MR imaging, cause the MR apparatus to:
load a measurement protocol for acquiring data of the examination object, the measurement protocol indicating a pulse sequence pattern and gradients to be applied in successive repetitions of the pulse sequence pattern,
acquire measurement data according to the measurement protocol by (i) determining, after each one of the successive repetitions in which a previous repetition included at least one gradient having an amplitude exceeding a predefined threshold value, at least one compensation gradient, and (ii) applying, via the one or more processors, the at least one compensation gradient following each one of the previous successive repetitions that included the at least one gradient having an amplitude exceeding the predefined threshold value; and
reconstruct image data using the acquired measurement data.

* * * * *